US008926997B1

(12) United States Patent
Stockel et al.

(10) Patent No.: US 8,926,997 B1
(45) Date of Patent: Jan. 6, 2015

(54) POLYMERIC BIOCIDAL SALTS

(76) Inventors: Richard F. Stockel, Bridgewater, NJ (US); Anthony J. Sawyer, Oakton, VA (US)

(*) Notice: Subject to any disclaimer, the term of this patent is extended or adjusted under 35 U.S.C. 154(b) by 377 days.

(21) Appl. No.: 12/798,479

(22) Filed: Apr. 5, 2010

Related U.S. Application Data

(63) Continuation-in-part of application No. 12/589,155, filed on Oct. 19, 2009, now abandoned, which is a continuation-in-part of application No. 11/633,231, filed on Dec. 4, 2006, now abandoned, which is a continuation-in-part of application No. 10/770,248, filed on Feb. 2, 2004, now abandoned.

(60) Provisional application No. 60/445,104, filed on Feb. 6, 2003.

(51) Int. Cl.
*A01N 25/00* (2006.01)

(52) U.S. Cl.
USPC .......................................................... 424/405

(58) Field of Classification Search
None
See application file for complete search history.

(56) References Cited

U.S. PATENT DOCUMENTS

| | | | | |
|---|---|---|---|---|
| 3,539,684 A | * | 11/1970 | Hoover ...................... | 424/78.35 |
| 3,567,420 A | * | 3/1971 | Legator et al. ................ | 504/160 |
| 3,825,560 A | | 7/1974 | Saito et al. ............... | 260/326.45 |
| 4,760,088 A | * | 7/1988 | Laks ............................. | 514/456 |
| 5,142,010 A | * | 8/1992 | Olstein ........................ | 526/248 |
| 5,149,524 A | * | 9/1992 | Sherba et al. .............. | 424/78.36 |
| 5,252,321 A | * | 10/1993 | Huth et al. ................. | 424/78.32 |
| 5,266,217 A | * | 11/1993 | Roe et al. ....................... | 210/764 |
| 5,780,658 A | | 7/1998 | Martinez-Prado et al. ..... | 554/51 |
| 5,869,073 A | * | 2/1999 | Sawan et al. ................. | 424/406 |
| 5,906,825 A | * | 5/1999 | Seabrook et al. ............. | 424/404 |
| 5,968,404 A | * | 10/1999 | Trinh et al. .................... | 252/8.91 |
| 6,030,632 A | * | 2/2000 | Sawan et al. ................. | 424/405 |
| 6,180,584 B1 | * | 1/2001 | Sawan et al. ................. | 510/382 |
| 6,264,936 B1 | * | 7/2001 | Sawan et al. ................. | 424/78.26 |
| 6,344,218 B1 | * | 2/2002 | Dodd et al. ................... | 424/605 |
| 6,458,348 B1 | * | 10/2002 | Tropsch et al. ............. | 424/78.35 |
| 6,491,840 B1 | * | 12/2002 | Frankenbach et al. ....... | 252/8.91 |
| 6,495,058 B1 | * | 12/2002 | Frankenbach et al. ....... | 252/8.91 |
| 6,528,013 B1 | * | 3/2003 | Trinh et al. ....................... | 422/5 |
| 6,554,620 B1 | * | 4/2003 | Iwai .............................. | 424/439 |
| 6,569,261 B1 | * | 5/2003 | Aubay et al. ..................... | 134/39 |
| 6,656,923 B1 | * | 12/2003 | Trinh et al. ....................... | 514/58 |
| 6,767,549 B2 | * | 7/2004 | Mandeville et al. ........... | 424/422 |
| 7,074,447 B2 | | 7/2006 | Bonaventura et al. ........ | 426/321 |
| 7,087,769 B1 | | 8/2006 | Mestres et al. .................. | 554/63 |
| 7,196,117 B2 | | 3/2007 | Beltran et al. ................ | 514/551 |
| 2002/0090349 A1 | * | 7/2002 | Bergeron et al. ........... | 424/70.11 |
| 2002/0102246 A1 | * | 8/2002 | Schneider et al. ............ | 424/94.4 |
| 2003/0211074 A1 | * | 11/2003 | Xianbin et al. ............. | 424/78.31 |
| 2004/0166082 A1 | | 8/2004 | Urgell-Beltran et al. ... | 424/70.21 |
| 2004/0175350 A1 | | 9/2004 | Beltran et al. ................ | 424/401 |
| 2004/0234492 A1 | * | 11/2004 | Stockel ....................... | 424/78.08 |
| 2004/0265443 A1 | * | 12/2004 | Beltran et al. ................ | 426/321 |
| 2005/0014932 A1 | * | 1/2005 | Imboden et al. .............. | 530/350 |
| 2005/0175747 A1 | | 8/2005 | Bonaventura et al. ........ | 426/335 |
| 2006/0177548 A1 | | 8/2006 | Sekula et al. .................. | 426/321 |

FOREIGN PATENT DOCUMENTS

| WO | WO 2007/014580 A1 | 8/2007 | ............. A61K 81/44 |
|---|---|---|---|
| WO | WO 2008/014824 A1 | 7/2008 | ............. A61K 31/16 |

OTHER PUBLICATIONS

MaRosa Infante, Aurora Pinazo and Joan Seguer. Non-conventional surfactants from amino acids and glycolipids: Structure, preparation and properties. Colloids and Surfaces A: Physicochemical and Engineering Aspects vols. 123-124, May 15, 1997, pp. 49-70.*

* cited by examiner

*Primary Examiner* — Robert A Wax
*Assistant Examiner* — Olga V Tcherkasskaya
(74) *Attorney, Agent, or Firm* — Posz Law Group, PLC

(57) ABSTRACT

A polymeric biocidal salt is prepared from two components. The first component comprises a biocidal anionic or cationic monomeric, dendrimeric or polymeric ion. The second component comprises a dendrimeric or polymeric anion or cation having insignificant biocidal activity and a number average molecular weight of at least about 500. The second component will be cationic in nature when the first component is anionic in nature and anionic in nature when the first component is cationic in nature. The salt is further characterized as partially dissolving when exposed to an aqueous medium, thereby:
 (a) releasing sufficient biocidal ion to exceed the MIC or MBIC of a target bacteria sought to be controlled; and
 (b) leaving a reservoir of undissolved salt capable of being further dissolved and releasing additional biocidal ion as the biocidal ion is consumed or is otherwise removed from the environment encompassing the target bacteria.

5 Claims, 1 Drawing Sheet

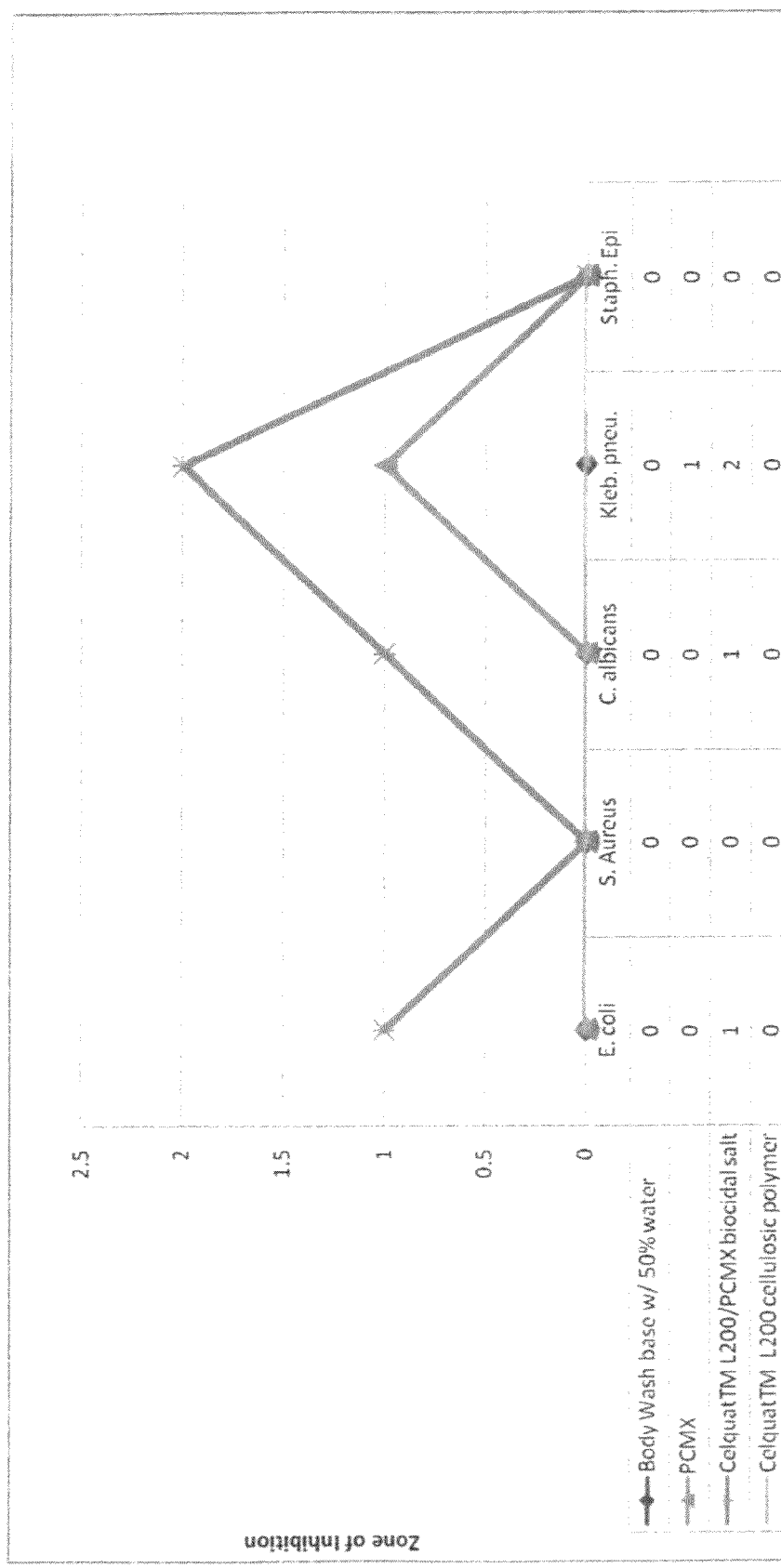

US 8,926,997 B1

POLYMERIC BIOCIDAL SALTS

REFERENCE TO RELATED APPLICATIONS

This application is a CIP application of U.S. Ser. No. 12/589,155, filed on Oct. 19, 2009, abandoned on Dec. 14, 2011, which is a CIP application of U.S. Ser. No. 11/633,231, filed on Dec. 4, 2006, abandoned on Jan. 1, 2010, which is a CIP application of U.S. Ser. No. 10/770,248, filed on Feb. 2, 2004, abandoned on Feb. 7, 2008, which claims priority to Provisional Application No. 60/445,104, filed on Feb. 6, 2003.

FIELD OF THE INVENTION

The invention relates to polymeric biocidal salts of two components: a first component comprising a biocidal anionic or cationic monomeric, dendrimeric or polymeric ion and a second component comprising a polymeric anion or cation having insignificant biocidal activity.

BACKGROUND OF THE INVENTION

The prior art describes a plethora of biocides for controlling microbiological organisms, gram-positive and gram-negative bacteria, molds, yeasts, etc. Although the prior art biocides are safe and efficacious for controlling such organisms, they are non-polymeric in nature and therefore the generally are short-lived in their activity, i.e., the prior art biocides generally do not have controlled-release or extended-release properties. Accordingly, such prior art biocides require multiple applications to keep the population of the microbiological organisms in check. Such multiple applications are not only annoying to the patient, but they often entail undesirable side effects due to the relatively high dosages that accumulate over their period of application. Moreover, for many applications, the prior art biocides lack substantivity, i.e., they do not readily adhere to the area to be treated.

OBJECTS OF THE INVENTION

It is an object of the invention to provide a relatively water-insoluble polymeric biocidal salt.

It is an additional object of the invention to provide a polymeric biocidal salt that will possess slow-release, i.e., extended-release, properties.

It is a further object of the invention to provide a polymeric biocidal salt that will exhibit substantivity, i.e., that the salt will adhere to skin and other surfaces such that biocide will be slowly released in and around the area to be treated.

The foregoing objects and other objects of the invention that will be apparent from the description set forth below have been achieved by the polymeric biocidal salts of the invention.

BRIEF DESCRIPTION OF THE DRAWING

FIG. 1 pertains to the results of in vitro testing of the polymeric biocidal salts of the invention using a zone of inhibition screening test.

DETAILED DESCRIPTION OF THE INVENTION

The invention pertains to a polymeric biocidal salt of a first component comprising a biocidal anionic or cationic monomeric, dendrimeric or polymeric ion and a second component comprising a dendrimeric or polymeric anion or cation having insignificant biocidal activity and a number average molecular weight of at least about 500. The second component is cationic in nature when the first component is anionic in nature and anionic in nature when the first component is cationic in nature. The salt is further characterized as partially dissolving when exposed to an aqueous medium, thereby:
(a) releasing sufficient biocidal ion to exceed the MIC or MBC of a target microbe sought to be controlled; and
(b) leaving a reservoir of undissolved salt capable of being further dissolved and releasing additional biocidal ion as the biocidal ion is consumed or is otherwise removed from the environment encompassing the target microbe.

The terms "MIC" and "MBC" employed in the description and the claims, refer to the Minimum Inhibitory Concentration and Minimum Bactericidal Concentration, respectively.

Preferably, the molar ratio of the first component to the second component is such that the salt will bear a charge ranging from a less than 50% negative charge to neutrality to less than a 50% positive charge. If a particular salt has a net positive charge of less than 50% in solution, it will generally be more substantive in respect to various surfaces and substrates than that of a salt having a charge ranging from neutrality to a net negative charge of less than 50% in solution. That is, the ionic sites on the second component may be saturated with ions of the first component or other non-functional counter-ions occupy some of the free ionic sites on the second component. Similarly, if the first component is polymeric in nature, the ionic sites of the polymeric first component may be saturated with ions of the second component or other non-functional counter-ions occupy some of the free ionic sites on the polymeric first component.

Typically, about 2 to about 500 ppm of biocidal ions are released when the salt is exposed to an aqueous medium such as water. This is quite ample for bactericidal applications. For example, about 2-8 ppm of chlorhexidine ("CHX") biocidal ions, about 1-8 ppm of cetyl pyridinium chloride ("CPC"), about 100-400 ppm of para-chloro-meta-xylenol ("PCMX") and about 2-40 ppm of triclosan biocidal ions are needed to inhibit or kill microbes such as bacteria, fungi and yeasts. However, this will vary with the antibacterial activity of the selected biocidal ion. Microbiological testing can be used to establish the MIC or MBC of a target microbe. Simple analyses can be used to determine the solubility of the biocidal salt and hence to establish its ability to provide continuous release as the biocidal ion is consumed or is otherwise removed from the environment encompassing the target microbe.

For those situations in which a very rapid inhibition or kill of a microbe is required, excess amounts of the first component can be provided together with the polymeric biocidal salt to rapidly sanitize the area to be treated.

The First Component

Preferably, the first component of the salt of the invention will comprise an anionic biocidal monomeric, dendrimeric or polymeric ion containing a functionality selected from the group consisting of phenolate; saturated, unsaturated or aromatic carboxylate; eneolate; dieneolate; mercaptide; dithio-alkylcarbamate; organophosphate; organophosphinate; organo-phosphonate; bis-phosphonate; organosulfate; and organosulfonate. Preferably, such ion is selected from the group consisting of the phenolate of triclosan; o-phenylphenolate; thymolate; eugenolate; the anion of 4-isopropyltropolone; undecylenate; the anion of mupirocin; a $C_8$-$C_{20}$ monoalkyl phosphate; a $C_8$-$C_{20}$ dialkyl phosphate; the anion of ethylenediaminotetrakis(methylenephosphonic acid); the anion of 2-mercaptopyridine N→oxide; salicylate; hexylresorcinolate; omadinate; bithionalate; dichloroacetate; stearate; mercaptobenzothiolate; dithiodimethyl carbamate; the diphenolate of hexachlorophene; 2,6-di-t-butyl-4-methylphenolate; the anion of 1-hydroxy-2-3-(3-pyridinyl)ethylidene-1,1-biphosphonic acid; an anion of a peptide; and anion of an amino acid.

Nonlimiting examples of suitable biocides that can generate such anionic biocidal monomeric, dendrimeric or polymeric ions include sodium salicylate; sodium hexylresorcinol; hydroxy carboxylic acid sodium salts; sodium omadine; disodium bithional; sodium dichloroacetate; sodium stearate; sodium mercaptobenzothiazole; sodium dithiodimethyl carbamate; sodium stearate; sodium undecylenate; sodium o-phenylphenol; disodium hexachlorophene; sodium triclosan; sodium 2,6-di-t-butyl 4-methylphenol; sodium tetraborate; chitosan derivatives containing carboxylate, sulfate, phosphonate or phosphate anions; ethylenediaminetetraacetic acid; ferulic acid ethylenediaminetetraacetic acid containing carboxylate anions; 1-hydroxyethane-1,1-diphosphonic acid; nitrilotris-(methylenephosphonic acid); ethylenediaminetetrakis(methylenephosphonic acid); monoalkyl phosphate; dialkyl phosphate; 1-hydroxy-2-(3-pyridinyl)-ethylidene-1,1-bisphosphonic acid, monosodium salt; an anionic peptide; and a basic amino acid.

Alternatively, the first component may comprise a cationic monomeric, dendrimeric or polymeric ion containing a functionality selected from the group consisting of amidine; guanidine; biguanide; quaternary amine; gemini quat; amine-acid salt of an antibiotic; and amine-acid salt of an azole.

Nonlimiting examples of suitable biocides that can generate such cationic biocidal monomeric, dendrimeric or polymeric ions include polyhexamethylene biguanide; polyhexamethylene guanidine; dimethyldidecyl ammonium; benzalkonium; benzethonium; chlorhexidine; poly(dimethylbutenyl ammonium chloride)-α,ω-bis(triethanolammonium chloride); propamidine; dibromo-propamidine; poly[oxyethylene(dimethylimino)ethylene(dimethylimino)] ethylene dichloride; dequalinium chloride; poly[bis(2-chloroethyl)ether-alt-1,3-bis[3-dimethylamino)propyl]urea, quaternized solution; hexetidine; cetyl pyridinium; tetrakis(hydroxymethyl)phosphoniumsulfate; tetrakis(hydroxymethyl)phosphonium chloride; ethanediyl-α,ω-bis(dodecyldimethyl)ammonium halide; a quaternary ammonium functionalized dendrimer; a $C_6$-$C_{20}$ sulfonium salt; a $C_6$-$C_{20}$ phosphonium salt; an antibiotic containing at least one amine salt; a triazole; an imidazole; a polyaminosaccharide salt; a cationic peptide; an acidic amino acid; p-chloro-m-xylenol; hexylresorcinol; 2,2'-methylenebis-(4-chloro-6-bromo-phenol); and a delmopinol salt.

Particularly useful cationic biocides are the $N^α$—($C_1$-$C_{22}$) alkanoyl dibasic amino acid alkyl ($C_1$-$C_{22}$) ester salts. Preferably, the di-basic amino acid is selected from the group consisting of arginine, lysine, histidine and tryptophan. An especially useful biocide is $N^α$-lauroyl-L-arginine ethyl ester. It should be noted that such biocides even at a pH of 10.0 have about 50% of the guanidine group still protonated. The alkanoyl and alkyl ester chain lengths can be varied to optimize the properties of such biocides depending on the desired end-use.

The Second Component

As stated above, the second component comprises a dendrimeric or polymeric anion or cation having insignificant biocidal activity and a number average molecular weight of at least about 500. The second component is cationic in nature when the first component is anionic in nature and anionic in nature when the first component is cationic in nature.

Preferably, the second component comprises a dendrimer or polymer that can generate the dendrimeric or polymeric anion or cation and is selected from the group consisting of:
(a) dendrimers containing functionalities selected from the group consisting of amino, phenolic, phosphate, phosphonate, sulfate, sulfonate, dithiocarbamate, mercapto, bis-phosphonate, bis phosphinate, carboxylate and mixtures of the foregoing functionalities;
(b) polyacrylates containing functionalities selected from the group consisting of amino, phenolic, phosphate, phosphonate, sulfate, sulfonate, dithiocarbamate, mercapto, bis-phosphonate, phosphinate, carboxylate and mixtures of the foregoing functionalities;
(c) polymethacrylates containing functionalities selected from the group consisting of amino, phenolic, phosphate, phosphonate, sulfate, sulfonate, dithiocarbamate, mercapto, bis-phosphonate, phosphinate, carboxylate and mixtures of the foregoing functionalities;
(d) polyethyleneimines;
(e) silicone polymers containing functionalities selected from the group consisting of amino, phenolic, phosphate, phosphonate, sulfate, sulfonate, dithiocarbamate, mercapto, bis-phosphonate, phosphinate, carboxylate and mixtures of the foregoing functionalities;
(f) styrenic polymers containing functionalities selected from the group consisting of amino, phenolic, phosphate, phosphonate, sulfate, sulfonate, dithiocarbamate, mercapto, bis-phosphonate, phosphinate, carboxylate and mixtures of the foregoing functionalities;
(g) diallyl dialkyl ammonium halide polymers;
(h) polysaccharides containing functionalities selected from the group consisting of amino, phenolic, phosphate, phosphonate, sulfate, sulfonate, dithiocarbamate, mercapto, bis-phosphonate, phosphinate, carboxylate and mixtures of the foregoing functionalities;
(i) polyvinyl amines;
(j) hyaluronic acid polymers;
(k) Polysulfonates;
(l) maleic acid homopolymers and copolymers;
(m) poloxazolines;
(n) polyphenols;
(o) polyamino acids;
(p) polypeptides;
(q) polyethylene glycols containing functionalities selected from the group consisting of amino, phenolic, phosphate, phosphonate, sulfate, sulfonate, dithiocarbamate, mercapto, bis-phosphonate, phosphinate, carboxylate and mixtures of the foregoing functionalities;
(r) polypropylene glycols containing functionalities selected from the group consisting of amino, phenolic, phosphate, phosphonate, sulfate, sulfonate, dithiocarbamate, mercapto, bis-phosphonate, phosphinate, carboxylate; and
(s) mixtures of the foregoing functionalities.

Polyphenols (and derivatives thereof) are indicated above as being compounds useful as the second component. Polyphenols are a group of chemical substances found in plants and are characterized by the presence of one or more phenolic units. Examples of suitable polyphenols are ferulic acid, reservatrol, gallic acid, coumaric acid, catechin, caffeic acid, vanillic acid, chlorogenic acid, aplanin and sinapyl arbutin. Additional useful second components are the pentacyclic triperpenoids, e.g., betulinic acid, moronic acid, ursolic acid and oleanolic acid.

Processes for the Preparation of the Salts

The salts of the invention may be prepared by either a metathesis or acid-base reaction as more particularly set forth below.

The Metathesis Reaction

As noted in the *McGraw-Hill Dictionary of Scientific and Technical Terms* (5th Edition, 1994), metathesis is a reaction involving the exchange of elements or groups as in the general reaction

$$AX + BY \longrightarrow AY + BX$$

The metathesis reaction is straight forward and can be readily carried out in aqueous solutions using water alone or a mixture of water and up to about 90 wt. % of a solvent such as a $C_1$-$C_4$ alcohol. If the polymeric biocidal salt is intended for use in an industrial application not involving any mammal or the preservation of food or a foodstuff, a wider choice of solvents is permissible. Typically, the solvent will be utilized in an amount of about 40 to about 80 wt. %, based on the weight of the entire reaction mixture. The metathesis reaction may be carried out at ambient temperature and is generally completed within one hour.

The choice of the first component will bear on the choice of the second component. For example, if the selected first component is an anionic monomeric, dendrimeric or polymeric biocidal ion, then the second component will be a cationic functional dendrimer or polymer ion having insignificant biocidal activity. Conversely, if the selected first component is a cationic monomeric or polymeric biocidal ion, then the second component will be an anionic functional dendrimer or polymer having insignificant biocidal activity.

An alkali or alkaline earth metal (e.g., Na, K, Li, Ca, etc.) salt of the selected biocidal anionic monomer, dendrimer or polymer is formed by reacting it with an equivalent amount of an alkali or alkaline earth metal hydroxide in water or a water-soluble polar or aprotic solvent or mixtures thereof. An acid salt of the selected cationic functional dendrimer or polymer having insignificant biocidal activity is formed by reacting it with an equivalent amount of an acid such as acetic, hydrochloric, hydrobromic, gluconic acid, sulfuric, etc. in water or a water-soluble polar or aprotic solvent or mixtures thereof.

The alkali or alkaline earth metal salt of the selected anionic monomeric, dendrimeric or polymeric biocide is then reacted with a molar amount of the acid salt of the cationic functional dendrimer or polymer having insignificant biocidal activity such that the resultant product, i.e., the polymeric biocidal salt of the invention, will bear a charge ranging from neutrality to less than 50% negative charge or less than 50% positive charge. The reaction mixture is stirred for several minutes up to about 1 hour at ambient temperature. The solid, i.e., the polymeric biocidal salt of the invention that precipitates from the reaction mixture, may be readily recovered by decantation of the supernatant layer (which contains the byproduct salts) or by filtration.

The polymeric biocidal salt of the invention, resulting from the metathesis reaction may be used as is for many of the applications described below. Alternatively, the salt may be dried in air or in an oven at moderate temperatures, e.g., 40 to 80° C. If desired, the salt may be further purified by recrystallization from a solvent or mixtures of solvents such as isopropanol, propylene glycol, dimethyl formamide, etc. The yield of the polymeric biocidal salt of the invention is excellent and is generally quantitative in nature.

The same procedure is used when preparing the polymeric biocidal salt of the invention using a cationic monomeric, dendrimeric or polymeric biocide and an anionic functional dendrimer or polymer having insignificant biocidal activity. In this situation, an acid salt of the selected biocide is reacted with an alkali or alkaline earth metal salt of the selected anionic dendrimer or polymer having insignificant biocidal activity. The same process parameters recited above are employed in this latter procedure.

One group of preferred polymers having insignificant biocidal activity consists of quaternary cellulosic compositions that can have one or more cellulosic functionalities per repeating unit. For example, Dow Chemical sells a line of quaternary cellulosics whose trade name is Softgel™. These materials are prepared by reacting cellulose with epichlorohydrin followed by the reaction with tertiary amines to form a quaternary moiety at the C6 position. Further reactions under more forceful conditions also can form a quaternary at position C1. In fact Softgel™ has both hydrophobic and hydrophilic quaternary groups leading to excellent cosmetic properties useful for hair or skin, e.g. substantivity, compatibility; etc. Another group of quaternary cellulosic polymers whose trade name is Celquat™ made by Akzo Nobel are actually grafted cellulose with diallyl dimethyl ammonium chloride. These also have excellent cosmetic properties, e.g. substantivity, etc., because of the conformal nature of the polymer that yields a coating for hair or skin.

Obviously saccharides other than cellulose having quaternary functionalities can be utilized, but cellulosics are preferred due to large scale availability and relative inexpensiveness compared to other systems.

Cationic polymers and monomers need to have a positive charge to react with an anionic species. There are certain cationic species both monomeric and polymeric that can maintain a certain degree of positive charge even at a neutral or slightly alkaline pH. This phenomenon is dependent on the isoelectric point which is where 50% of the species are protonated and 50% are non-protonated. A polymeric example is polyethyleneimine which at a pH of 8.0 still has about 30% of its amino groups protonated.

The Acid-Base Reaction

It is preferred to use the acid-base reaction to prepare the polymeric biocidal salts of the invention rather than the metathesis reaction since the acid-base reaction does not result in by-product salts that must be disposed of in an environmentally sound manner. However, in order to prepare the polymeric biocidal salts of the invention by an acid-base reaction, it is necessary that the selected anionic monomeric, dendrimeric or polymeric biocide be present in the form of its free base having a $pK_b$ numerical value of at least about 6 and the cationic functional polymer having insignificant biocidal activity be present in the form of its undissociated acid having a $pK_a$ numerical value of about 8 or less. Alternatively, the selected cationic monomeric, dendrimeric or polymeric biocide must be present in the form of its acid having a $pK_a$ numerical value of about 8 or less and the anionic functional dendrimer or polymer having insignificant biocidal activity that is present in the form of its free base having a $pK_b$ numerical value of at least about 6.

The acid-base reaction is typically carried out in the presence of about 40 to about 80 wt. % of a solvent consisting of a $C_1$-$C_4$ alcohol or a mixture of about 20 to about 60 wt. % water and such alcohol. The reaction mixture is generally stirred under reflux for about 30 minutes to about 10 hours and the reaction product, i.e., the polymeric biocidal salt of the invention, is recovered by evaporation of the solvent. If desired, the reaction product may be recrystallized using a solvent or a mixture of solvents such as isopropanol, propylene glycol, dimethyl formamide, etc., or with small amounts of water.

As in the case of the metathesis reaction, the molar ratio of the first component to the second component is such that the polymeric biocidel salt of the invention will bear a charge ranging from less than 50% negative charge to neutrality to less than 50% positive charge.

The acid-base reaction may be illustrated by the following equation:

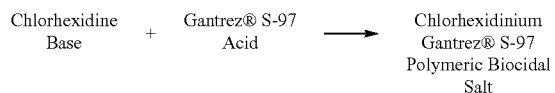

Chlorhexidine Base + Gantrez® S-97 Acid → Chlorhexidinium Gantrez® S-97 Polymeric Biocidal Salt Gantrez® S-97 is the free acid of a copolymer of methyl vinyl ether having the CAS number of 25153-40-69. It is available from International Specialty Products and is typically supplied as a free-flowing powder or as a slightly hazy, viscous liquid. The approximate weight average molecular weight of the copolymer is 1,200,000-1,500,000.

Emulsions/Microemulsions of the Salts

The polymeric biocidal salts of the invention typically have limited water solubility. Accordingly, for many of the applications recited hereinbelow, it is desirable to utilize the salts in the form of emulsions or microemulsions. The following is a generalized procedure for preparing emulsions or microemulsions of the polymeric biocidal salts of the invention.

Initially, the polymeric biocidal salt is dissolved in the minimum amount of a solvent that will completely dissolve the selected salt in an amount that is appropriate for use in the desired application. The solvent of choice will be one with the appropriate Hildebrand solubility parameter. The solubility parameter is a numerical value that indicates the relative solvency behavior of a specific solvent. Hildebrand solubility parameters of about 8.5 to about 22.0 are generally suitable for solubilization of the polymeric biocidal salts of the invention. Exemplary solvents with the requisite Hildebrand solubility parameters include isopropanol, propylene glycol, sorbitol, glycerin, dimethyl formamide, and the like.

The desirable Hildebrand solubility parameter will depend on the ionic/covalent bonding energies of the polymeric biocidal salts. The correct solvent will be one having a relatively low Hildebrand solubility parameter if the bonding has more covalency and a relatively high Hildebrand solubility parameter if the bonding is more ionic. Of course, combinations of correct solvents may also be utilized to dissolve the salts of the invention.

The Surfactants

After the salt has been dissolved, a surfactant is added to the solution. The surfactant may be cationic, anionic or amphoteric in nature, and combinations of the different types or combinations of the same type of surfactants may be use. Preferably, the surfactant will be amphoteric or nonionic in nature. Highly negative anionic surfactants are not very functional. Many of them will react with cationic biocides making them insoluble and therefore inactive. Alternatively, they can react with cationic functional polymers used as the second component. The last step is to dilute the salt-solvent-surfactant composition with water to the concentration desired for the selected application so as to form an emulsion or microemulsion, depending on the micellar size and the choice of solvents/cosolvents.

Cationic phospholipids, preferably in combination with nonionic and/or amphoteric surfactants are effective in the formation of emulsions or microemulsions of the polymeric biocidal salts of the invention. Surfactants that carry a positive charge in strongly acidic media carry a negative charge in strongly basic media, and form zwitterionic species at intermediate pH levels are amphoteric. The preferred pH range for stability and effectiveness is about 5.0 to about 9.0. Within this pH range, the amphoteric surfactant is mostly or fully in the zwitter (neutral) form, thereby negating any dilution of biocidal activity of the polymeric biocidal salts of the invention, provided that the surfactant is employed in the preferred concentration range of about 0.25 to about 10.0 wt. %, based on the weight of the polymeric biocidal salt.

The following surfactants have been found to be effective in the formation of microemulsions or semi-transparent emulsions of the polymeric biocidal salts of the invention: amphoteric amidobetaines; nonionic polyethoxylated sorbitol esters, polycondensates of ethylene oxide-propylene oxides (polyoxamers), polyethoxylated hydrogenated castor oils, and certain cationic phospholipids.

Suitable examples of amidobetaines include cocoamidoethyl betaine, cocoamidopropyl betaine; and mixtures thereof. Other suitable amphoteric surfactants include long chain imidazole derivatives such as the product marketed under the trade name "Miranol C2M" by Rhodia and long chain betaines such as the product marketed under the trade name "Empigen BB" by Huntsman Corporation, and mixtures thereof.

Suitable nonionic surfactants include polyethoxylated sorbitol esters, especially poly-ethoxylated sorbitol monoesters, e.g., PEG sorbitan diisostearate, and the products marketed under the trade name "Tween" by ICI; polycondensates of ethylene oxide and propylene oxide (polyoxamers), e.g., the products marketed under the trade name "Pluronic" by BASF; condensates of propylene glycol; polyethoxylated hydrogenated castor oil such as the products marketed under the trade name "Cremophors" by BASF; and sorbitan fatty esters marketed by ICI. Other effective nonionic surfactants include the polyalkyl ($C_8$-$C_{18}$) glucosides.

Suitable cationic surfactants include D,L-pyrrolidone-5-carboxylic acid salt of ethyl-cocoyl-L-arginate (CAE) marketed by Ajinomoto, and cocoamidopropyl and lauramidopropyl PG dimonium chloride phosphates and the like marketed by Croda.

Applications

The following is a representative list of some of the numerous possible applications of the polymeric biocidal salts of the invention. It should be understood that this list is presented for illustrative purposes only and does not represent any limitation as to possible applications. It should be further understood that it is within the purview of this invention that the products described below, which contain the polymeric biocidal salts of the invention, may also contain other formulation ingredients, such as conventional antioxidants, antibacterial agents, antifungal agents, hormones, vitamins, antioxidants, hydroxy acids, cleansers, soaps, shampoos, silicones, biocides, humectants, emollients, synthetic or natural oils, deodorizers, perfumes, colorants, preservatives, plant extracts, etc.

(1) skin and hair care products, e.g., sunscreens; suntan lotions; after-sun gels, lotions and creams; antiperspirants;

deodorants (solutions, powders, gels, roll-ons, sticks, sprays, pastes, creams, lotions); cleansing creams; skin conditioners; skin moisturizers; protectants; skin aging products; skin wrinkle reduction products; products for treatment of acne; products for treatment of rosacea; age-spot reduction products; stretch-mark reduction products; pimple treatment products, skin soothing products; skin infection and lesion treatment products; skin-redness reduction products; stretch-mark reduction products; varicose and spider-vein reduction products; lotions; oils; hand/body creams; shaving gels/creams; body washes; liquid and solid soaps; blood microcirculation improvement products, cellulite reduction products, body toning products, skin penetration enhancers; skin whitening products; cosmetics; shampoos; shower gels; bubble baths; hair treatment products, e.g., medicated shampoos, mousses, waxes, conditioners, styling agents, lotions, pomades, spray gels, hair dyes and tints, colorant and non-colorant rinses, detangling lotions, hair curling and hair straightening products, hair wave products, etc.; hand (or mechanical) dishwashing compositions; lipsticks and lip balms; salves; collodion; impregnated patches and strips for skin treatment; skin surface implants; impregnated or coated diapers; and the like.

(2) dental care materials: mouthwash; dentifrice; dental floss coated or impregnated with the polymeric biocidel salt; protective coating for teeth; toothbrush bristles coated or impregnated with the polymeric biocidal salt; orthodontic appliance coated or impregnated with the polymeric biocidal salt; orthodontic appliance adhesive; denture appliance coated or impregnated with the polymeric biocidal salt; denture appliance adhesive; endodontic composition coated or impregnated with the polymeric biocidal salt; composite-type dental restorative materials; dental cement; dental liner; dental bonding agent; and the like.

(3) foods and food products: food-stuffs; animal feed-stuffs; grains; breads; bakery products; confectionary; potato products; pasta products; salads; soups; seasonings; condiments; syrups; jams, jellies and marmalades; dairy products; egg-based products; meats and meat-based products; poultry and poultry-based products; fish and fish-based products; crustaceans and crustacean-based products; fresh and dried fruit products; vegetables and vegetable products; greens; salads; sauces; beverages, e.g., wines, tea extracts, beers, juices; and the like.

(4) plastics and miscellaneous products where the salts of this invention are coated or impregnated or incorporated in the item: medical items, e.g., thermometers, catheters, surgical sutures, blood lines, implants, bandages, surgical dressings, surgical apparel, respirators, etc.; food packaging; drug and cosmetic packaging; eating utensils; shower curtains; bath mats; sponges; mops; toilet seats, rubber gloves; contact lenses; hearing aids; shelving paper; carpet pads; pool covers; animal bedding and cat litter; computer covers and computer keys; doorknobs; tampons and sanitary napkins; dental chairs; dryer sheets; dishcloths; paints and coatings; powdered, liquid, gel and spray cleaners for floors sinks, countertops, walls, tiles, floors, carpets; deodorizing liquids, solids, sprays, gels and powders; filters; foams; hair brushes; combs; adult novelties; sexual aids; sex toys; condoms; pregnancy barriers; and the like.

(5) fibers and fabrics wherein the polymeric biocidal salts of the invention are coated or impregnated or incorporated in the item: natural and synthetic fibers and fabrics manufactured from such fibers; wipes, cloths; surgical gauze; crib covers; bassinet covers; bed linens; towels and wash cloths; tents; draw sheets; cubicle curtains; shower curtains; wall coverings; wood and wood products; hospital clothing such as examination robes, physicians' coats, nurses uniforms, etc.; apparel; shoes and the like The following nonlimiting examples shall serve to illustrate the embodiments of the invention. Unless otherwise indicated, all parts and percentages are on a weight basis.

Example 1

A polymeric biocidal salt was prepared from sodium triclosan and polyethyleneimine hydrochloride salt by the metathesis reaction as described above. A 10.7 wt. % solids formulation dilutable with water was prepared from the following ingredients:
20 g polymeric biocidal salt
150 g glycerin
1.5 g cocoamidopropyl betaine Example 2

A polymeric biocidel salt was prepared from dimethyldidecyl ammonium chloride and a polyethylene glycol terminated with a carboxylate by the metathesis reaction as described above. A 19.41 wt. % solids formulation dilutable with water was prepared from the following ingredients:
20 g polymeric biocidal salt
200 g sorbitol
3.0 g cocoamidopropyl betaine Example 3

A polymeric biocidal salt was prepared from chlorhexidine base and Gantrez® S-97 by the acid-base reaction as described above. A 10.0 wt. % solids formulation dilutable with water was prepared from the following ingredients:
20 g polymeric biocidal salt
180 g propylene glycol
2 g polyoxyethylene sorbitan monolaurate (CAS #9005-64-5)
2 g cocoamidopropyl betaine Example 4

The bacteriostatic activity of the polymeric biocide salts of Examples 1-3 was tested at 0.1 wt. % using "Oxoid" No. 2 nutrient broth and inoculating the broth with 1 ml of a 24-hour broth culture of the test organisms listed below after incubation at the optimum growth temperature of the organism for 48 hours. The organisms tested were:
*Pseudomonas aureus* (gram positive)
*Pseudomonas aeruginosa* (gram negative)
*Escherichia coli* (gram negative)

The salts of Examples 1, 2 and 3 were found to be bacteriostatic at 0.1 wt % against each of the above organisms.

The substantivity testing in vitro/zone of inhibition screening test as depicted in FIG. 1 can be used to screen antimicrobial compounds and determine their effectiveness. The purpose of the test is to determine whether residual antimicrobial compound is retained on a selected surface in a quantity sufficient to inhibit microbial growth. The method for conducting the test is as follows: The products to be tested are diluted with water (2 g product+8 g water) and mixed and soaked with cotton swatches for one minute. The cotton swatches are then thoroughly rinsed with water and patted dry on paper towels. The resultant swatches are then placed on surface streaked tryptic soy agar plates, incubated and the zone is measured and recorded. The size of the zone may or may not be a measure of the strength of the antimicrobial compound. The zone, if any, is then graded as follows:

0=no zone
1=minimal
2=1 mm
3=2 mm
4=3-5 mm
5=complete clearing

The results of the test are depicted in FIG. 1 in which various materials were tested against *Escherichia coli* ("*E. coli*") *Staphylococcus aureus* ("*S. aureus*"), *Candida albicans* ("*C. albicans*"), *Klebsiella pneumonia* ("*Kleb. pneu.*") and Staphylococcus epidermis ("*Staph. Epi*"). The materials subjected to the screening test were as follows:

"Body Wash base": "Colgate® Men's Active (blue)" 50% diluted with distilled water.

"PCMX": para-chloro-meta-xylenol

"Celquat™L200/PCMX biocidal salt": a polymeric biocidal salt of the invention prepared by the metathesis reaction of the anion of sodium para-chloro-meta-xylenol and Celquat™L200, a cellulosic non-biocidal quaternary cationic polymer.

"Celquat™L200": a cellulosic non-biocidal quaternary cationic polymer.

"Liquid hand soap containing 0.15% triclosan".

As may be seen from the results depicted in FIG. 1, there is an improvement in the substantivity the Celquat™L200/PCMX biocidal salt of the invention versus PCMX in respect to all of microbes. The Body Wash base had no effect on the inhibition of the microbes. Only the Celquat™L200/PCMX biocidal salt of the invention, PCMX and the liquid hand soap containing 0.15% triclosan exhibited any antimicrobial activity.

The preceding specific embodiments are illustrative of the invention. It is, however, to be understood that other expedients known to those skilled in the art or disclosed herein may be employed without departing from the spirit of the invention or the scope of the claims which follow.

What is claimed is:

1. A polymeric biocidal salt of
   (1) a biocidal monomeric cationic component selected from the group consisting of a $N^\alpha$-lauroyl-L-arginine ethyl ester, chlorhexidine, and cetyl pyridinium and a polymeric anionic component selected from the group consisting of an acrylate, hyaluronic acid and a copolymer of methyl vinyl ether and maleic anhydride; or
   (2) a polymeric cationic component poly(diallyldimethyl ammonium chloride) and a biocidal monomeric anionic component p-chloro-m-xylenol,
   and wherein said salt exposed to an aqueous medium
   (a) releases from about 2 ppm to about 500 ppm of biocidal ions; and
   (b) releases additional biocidal ions when consumed biocidal ions are removed from the environment.

2. The salt of claim 1 formed by a metathesis reaction between:
   (i) an acid salt of a biocidal monomeric cationic component and an alkali or alkaline earth metal salt of a polymeric anionic component; or
   (ii) an acid salt of a polymeric cationic component and an alkali or alkaline earth metal salt of an biocidal monomeric anionic component.

3. The salt of claim 1 formed by an acid-base reaction between:
   (i) an biocidal anionic component in the form of free base and having a $pK_b$ value of about 6 or more and a polymeric cationic component in the form of undissociated acid having a $pK_a$ of about 8 or less, or
   (ii) a biocidal cationic component in the form of free acid and having a $pK_a$ of about 8 or less and a polymeric anionic component in the form of free base having a $pK_b$ value of about 6 or more.

4. An emulsion/microemulsion comprising:
   (i) a salt of claim 1;
   (ii) a solvent with Hildebrand solubility parameters of about 8.5 to about 22.0;
   (iii) an amphoteric or nonionic surfactant.

5. A material containing the salt of claim 1, wherein said material is selected from the group consisting of a food or food product; a beverage; a preservative composition; a perishable item; a packaging; a plastic; a pharmaceutical product; a medical device, a cosmetic; a deodorant; a coating; a dental care composition; a dental care appliance; a dental hygiene product; a wound care composition; a dermatological care composition; a personal hygiene item; an adult novelty item; a sexual aid item; a sex toy item; a condom item; a pregnancy barrier item; an infant care product; a surgical soap; a surgical or hospital gown; a microbiocide; an antifungal composition; an anti-yeast composition; an anti-mold composition; an animal care product; an apparel product; a woven or nonwoven or knit fabric; a foam; a film; a paper product; a construction material; plasterboard; a rubber item; and a virucide.

\* \* \* \* \*